(12) United States Patent
Cobbs et al.

(10) Patent No.: US 8,706,515 B2
(45) Date of Patent: *Apr. 22, 2014

(54) METHODS, SYSTEMS, AND APPARATUS FOR PROVIDING A NOTIFICATION OF A MESSAGE IN A HEALTH CARE ENVIRONMENT

(75) Inventors: Archie Cobbs, Birmingham, AL (US); Paul Gartman, Birmingham, AL (US)

(73) Assignee: McKesson Information Solutions LLC, San Francisco, CA (US)

( * ) Notice: Subject to any disclaimer, the term of this patent is extended or adjusted under 35 U.S.C. 154(b) by 1624 days.

This patent is subject to a terminal disclaimer.

(21) Appl. No.: 11/255,115

(22) Filed: Oct. 20, 2005

(65) Prior Publication Data

US 2007/0094045 A1    Apr. 26, 2007

(51) Int. Cl.
*G06Q 50/00*    (2012.01)
*G06Q 10/00*    (2012.01)

(52) U.S. Cl.
USPC .................................................. 705/2; 705/3

(58) Field of Classification Search
USPC ........................................................ 705/2–3
See application file for complete search history.

(56) References Cited

U.S. PATENT DOCUMENTS

| | | |
|---|---|---|
| 4,135,241 A | 1/1979 | Stanis et al. |
| 4,807,155 A | 2/1989 | Cree et al. |
| 4,994,908 A | 2/1991 | Kuban et al. |
| 5,319,363 A | 6/1994 | Welch et al. |
| 5,331,549 A | 7/1994 | Crawford et al. |
| 5,452,808 A | 9/1995 | Abramowitz |
| 5,713,350 A | 2/1998 | Yokota et al. |
| 5,748,907 A | 5/1998 | Crane |
| 5,760,704 A | 6/1998 | Barton et al. |
| 5,781,442 A | 7/1998 | Engleson et al. |
| 5,802,494 A | 9/1998 | Kuno |
| 5,946,659 A | 8/1999 | Lancelot et al. |

(Continued)

FOREIGN PATENT DOCUMENTS

| | | |
|---|---|---|
| EP | 1 310 895 A2 | 5/2003 |
| WO | WO 91/06917 A | 5/1991 |

(Continued)

OTHER PUBLICATIONS

"Subnotebooks, Phones and More. St. Vincent's Gets on Track," Mobile Health Data [Online], pp. 1-2, Nov. 19, 2004, obtained from http://www.awarix.com on Jul. 2, 2007.

(Continued)

*Primary Examiner* — Minnah Seoh
(74) *Attorney, Agent, or Firm* — Sutherland Asbill & Brennan LLP

(57) ABSTRACT

The disclosure relates to methods, systems, and apparatus for providing a notification of a message in a health care environment. A message from a source and location information associated with a plurality of patients may be received. The location information associated with the plurality of patients and a notification of the message from the source may be output in a geospatial arrangement via a graphical user interface. The graphical user interface may be updated when a change occurs in either the location information associated with at least one of the plurality of patients or the status of the message from the source. In addition, a user query for the location information associated with each of the plurality of patients receiving care from a physician in the health care environment may be received and output in the geospatial arrangement via the graphical interface.

21 Claims, 6 Drawing Sheets

(56) References Cited

U.S. PATENT DOCUMENTS

| | | | |
|---|---|---|---|
| 6,078,261 A | | 6/2000 | Davsko |
| 6,314,556 B1 | | 11/2001 | De Busk et al. |
| 6,356,874 B1 | | 3/2002 | Øhrn et al. |
| 6,662,050 B2 | | 12/2003 | Olson |
| 6,701,345 B1 | | 3/2004 | Carley et al. |
| 7,716,066 B2 | | 5/2010 | Rosow et al. |
| 7,720,695 B2 | | 5/2010 | Rosow et al. |
| 7,734,479 B2 | | 6/2010 | Rosow et al. |
| 7,756,723 B2 | | 7/2010 | Rosow et al. |
| 7,774,215 B2 | | 8/2010 | Rosow et al. |
| 7,890,347 B2 | | 2/2011 | Rosow et al. |
| 7,953,610 B2 | | 5/2011 | Rosow et al. |
| 2001/0042135 A1 | * | 11/2001 | Lewis .................. 709/246 |
| 2002/0013714 A1 | | 1/2002 | Dubler et al. |
| 2002/0042745 A1 | | 4/2002 | Nacey |
| 2002/0044043 A1 | | 4/2002 | Chaco et al. |
| 2002/0091309 A1 | | 7/2002 | Auer |
| 2002/0116226 A1 | | 8/2002 | Auer et al. |
| 2002/0158919 A1 | | 10/2002 | Nacey |
| 2002/0183979 A1 | * | 12/2002 | Wildman .................. 702/188 |
| 2003/0074222 A1 | * | 4/2003 | Rosow et al. .................. 705/2 |
| 2003/0078810 A1 | | 4/2003 | Cole et al. |
| 2003/0078811 A1 | | 4/2003 | Cole et al. |
| 2004/0046020 A1 | | 3/2004 | Andreasson et al. |
| 2004/0078231 A1 | | 4/2004 | Wilkes et al. |
| 2004/0167804 A1 | | 8/2004 | Simpson et al. |
| 2004/0243446 A1 | | 12/2004 | Wyatt |
| 2005/0219059 A1 | | 10/2005 | Ulrich et al. |
| 2005/0242946 A1 | | 11/2005 | Hubbard et al. |
| 2005/0283382 A1 | | 12/2005 | Donoghue et al. |
| 2006/0004605 A1 | * | 1/2006 | Donoghue et al. ............ 705/2 |
| 2006/0049936 A1 | | 3/2006 | Collins, Jr. et al. |
| 2006/0114888 A1 | | 6/2006 | Schuman |
| 2006/0143045 A1 | | 6/2006 | Nacey |
| 2006/0167738 A1 | | 7/2006 | Spear et al. |
| 2006/0247948 A1 | | 11/2006 | Ellis et al. |
| 2007/0094046 A1 | | 4/2007 | Cobbs et al. |
| 2008/0164998 A1 | | 7/2008 | Scherpbier et al. |
| 2009/0315735 A1 | | 12/2009 | Bhavani et al. |
| 2013/0311516 A1 | | 11/2013 | Callans et al. |

FOREIGN PATENT DOCUMENTS

| | | |
|---|---|---|
| WO | WO 97/25682 A | 7/1997 |
| WO | WO 98/50871 A | 11/1998 |
| WO | 2007047052 A2 | 4/2007 |

OTHER PUBLICATIONS

"Coping with Information Overload," The News Source for Healthcare Information Technology [Online], pp. 1-2, Nov. 2004, obtained from http://www.awarix.com on Jul. 2, 2007.

St. Vincent's first to use Birmingham startup's information system, The Birmingham News [Online], pp. 1-3, Apr. 11, 2005, obtained from http://www.awarix.com on Jul. 2, 2007.

D Lockridge, "St. Vincent's is Digital Flagship," Birmingham Medical News [Online], pp. 1-3, Sep. 2005, obtained from http://www.awarix.com on Jul. 2, 2007.

"Two Automatic Identification Technology, neither new in the sense of being recent developments . . . ," Patient Safety & Quality Healthcare [online], pp. 1-4, Aug. 2005, obtained from http://www.awarix.com on Jul. 2, 2007.

G.M. Jacquez et al., "Design and Implementation of Space-Time Intelligence System for Disease Surveillance," Journal of Geographical Systems: Geographical Information, Analysis, Theory and Decision, Springer-Verlag, BE, vol. 7, No. 1, pp. 7-23, May 1, 2005.

International Search Report and Written Opinion for PCT/US2006/037573, issued Jan. 17, 2007.

Enterprise Patient Care Visibility Solutions, Patient Care Communication Board, Awarix, Inc., http://www.awarix.com/products.html.

International Search Report and Written Opinion for PCT/US2006/037755, issued Aug. 27, 2007.

Final Office Action for U.S. Appl. No. 11/255,145 mailed Sep. 16, 2009.

Non-Final Office Action for U.S. Appl. No. 11/255,145 mailed May 27, 2009.

Disclosure Statement Under 37 C.F.R. § 1.56 for U.S. Appl. No. 11/255,115.

Non-Final Office Action for U.S. Appl. No. 11/255,145 mailed Jan. 26, 2012.

Final Office Action for U.S. Appl. No. 11/255,145 mailed May 31, 2012.

Non-Final Office Action for U.S. Appl. No. 11/255,145 mailed Jun. 19, 2013.

International Search Report and Written Opinion for PCT/US2012/025158, issued Jun. 12, 2013.

Notice of Allowance for U.S. Appl. No. 12/255,145 mailed Dec. 16, 2013.

* cited by examiner

METHODS, SYSTEMS, AND APPARATUS FOR PROVIDING A NOTIFICATION OF A MESSAGE IN A HEALTH CARE ENVIRONMENT

FIELD OF THE INVENTION

The invention relates generally to the field of health care, and more particularly, relates to methods, systems, and apparatuses for providing a notification of a message in a health care environment.

BACKGROUND OF THE INVENTION

Various health care environments such as hospitals or assisted care facilities can involve relatively complex information and associated work flows. Health care workers can serve in a wide variety of roles and work in many different physical locations across a hospital or other enterprise. Some workers, such as physicians, can be very mobile. As may be expected in such environments, effective communication among workers can be an essential requirement for the overall operation to be coherent and productive.

Different types of communication in a hospital or other enterprise can be measured along a spectrum of urgency. For example, urgent-type messages can often be delivered via a paging system or walkie-talkie type device. Non-urgent-type messages can be delivered via e-mail or voice mail. Other technologies such as beepers and overhead paging systems (for urgent-type messages), and laptop computers and telephones (for non-urgent-type messages) also exist. An example of an urgent-type message can include a nurse notifying a doctor of an urgent medical condition. Non-urgent-type messages can include a general notification of an upcoming scheduled maintenance, a request for replenishment of material resources, or the like.

In a health care environment, such as a hospital, there can also be many "medium urgency"-type messages. Medium urgency-type messages can require attention as soon as possible, but not immediately. Examples of medium urgency-type messages in a health care environment can include nurse-to-nurse reports posted before transferring a patient between units, non-urgent requests for information or clarification between nurses and doctors, requests for an unscheduled room cleaning, and the like.

However, for medium urgency-type messages there are relatively fewer suitable technologies. Voice mail and e-mail are oftentimes not checked by the recipient, or in some instances ignored, due to the time and effort required to check and receive the voice mail or e-mail. In addition, the recipient must "poll" for messages. That is, the recipient may not know whether any voice mail or e-mails exist until he or she actually checks. With voice mail, and typically with e-mail as well, a sender may not know whether the recipient has received the voice mail or e-mail. On the other hand, medium urgency-type messages should not result in interrupting a recipient from his or her current task, such as would happen with a page or walkie-talkie voice conversation. Telephone calls are oftentimes relatively worse, as such communications behave like a walkie-talkie conversation with a relatively longer initial delay, or may revert to a voice mail, but without the caller knowing prior to the call whether the call will result in a direct conversation with the recipient or whether a voice mail will have to be left for the recipient.

Therefore, a need exists for methods, systems, and apparatuses for providing a notification of message in a health care environment.

A further need exists for methods, systems, and apparatuses for providing a notification of a voice message in a health care environment.

Yet a further need exists for methods, systems, and apparatuses for providing message notifications associated with care of a patient in a health care environment.

SUMMARY OF THE INVENTION

Some or all of the needs can be addressed by embodiments of the present invention. Embodiments of the present invention can improve communications and information flow in a health care environment, such as a hospital or assisted care facility, using one or more graphical user interfaces located within the health care environment, such as on walls, in patient rooms, and adjacent to areas where health care personnel may work or otherwise be stationed. Such interfaces can display various pieces of graphical-type information in a geospatial arrangement such as a map, including the status of rooms and patients in the patient care or nursing units, a patient's location, an indicator of care of the patient, a status of rooms in a particular area or department. The information provided by such graphical user interfaces can be readily available to a user or health care personnel and can be updated in real time as a change to the information is made, detected, or otherwise received by the present invention. Information that may otherwise require making a telephone call or sitting down and logging in to some computer application to retrieve the information can be readily available via the display screen and updated in real time. Such display screens can be associated with a variety of processor-based platforms including mobile handheld portable computers and desktop computers.

In some instances, users may be interested in sending and receiving medium urgency-type messages in a health care environment. One embodiment of the present invention combines interactive voice response (IVR)-type functionality with voice mail-type functionality in a communication system with one or more graphical user interfaces located within the health care environment. The communication system can receive, record, and deliver a message or other communication, and the graphical user interface can provide a notification to a recipient to retrieve the message or other communication.

In other instances, users may be interested in obtaining specific information, and can submit a user query for selected information via a computer system. Other types of queries can be based at least in part on contextual-type information associated with a user or a patient, such as a user's role, or a location of a particular client device. Frequently used queries can be stored, formatted, and retrieved by a user for subsequent use. Information received in response to a user query can be graphically displayed via a graphical user interface in a graphical representation. The graphical representation permits information to be displayed with relatively greater information density, and permits users to rapidly view and comprehend such information. Various graphical views of the information can be displayed and updated in real time to show changes in events and activities associated with care of the patients.

One aspect of the invention can include a method for providing a message notification associated with care of a patient in a health care environment. The method can include receiving a message from a source, and receiving location information associated with a patient. The method also includes outputting in a geospatial arrangement via a graphical user interface the location information associated with the patient, and a notification of a message from the source. In addition, the method includes updating the graphical user interface when a change occurs in either the location information associated with the patient or status of the message from the source.

Another aspect of the invention can include a method for providing a message in a health care environment. The method can include receiving information associated with a patient in a health care environment, wherein the information can include a message from a source. The method also includes outputting via a graphical user interface a geospatial arrangement of information associated with the patient and a status of the message from the source. In addition, the method includes transmitting the message to a user. Furthermore, the method includes updating the status of the message from the source displayed by the graphical user interface when the user receives the message.

Yet another aspect of the invention can include a system for providing a message notification associated with care of a patient in a health care environment. The system can include an output device capable of displaying a geospatial arrangement for a graphical user interface, a location associated with a patient and a status of a message from a source. The system can also include a message notification engine capable of receiving a message from a source. The message notification engine is further capable of receiving information associated with the patient in a health care environment, wherein the information can include a location associated with the patient. In addition, the message notification engine is further capable of outputting in a geospatial arrangement via a graphical user interface for an output device the location associated with the patient and a status of the message from the source. The message notification engine is further capable of providing access to a user to receive the message from the source. In addition, when a change in the status of the message from the source occurs, the message notification engine is further capable of updating the graphical user interface.

Another aspect of the invention can include a user interface for providing a message notification associated with care of a patient in a health care environment. The user interface can include a geospatial view of a health care environment. In addition, the user interface can include at least one indicator associated with a location of a patient in the health care environment, and at least one indicator of a message from a source.

Other embodiments of the invention can provide information associated with care of a patient in a health care environment. Yet other embodiments of the invention can provide a notification of a message in a health care environment. Still other embodiments of the invention can provide a visible notification of a voice communication associated with care of a patient in a health care environment. In addition, other embodiments of the invention can provide notifications of communications associated with care of the patient in a health care environment. In addition, other embodiments of the invention can provide a user interface for providing notifications of communications associated with care of a patient in real time in a health care environment.

An aspect of an embodiment of the invention can include asynchronous-type delivery of messages or other communications. That is, a recipient does not need to be involved or present when the message is created. An additional aspect of an embodiment of the invention can further include immediate notification of a sender and/or recipient, wherein a message notification can be automatically posted immediately where a recipient can notice it and a sender can monitor the status of the notification. In addition, an aspect of an embodiment can include relatively minimally invasive notifications that minimize disruption of a recipient from his or her current task or minimize disruptions to the patient care or health care environment. Another aspect of an embodiment can include a relatively low cost notification, wherein a message notification can avoid being skipped or otherwise ignored by a recipient due to the cost associated with noticing them. Yet another aspect of an embodiment can include message time information, wherein a recipient can determine how old a particular message or communication is. One other aspect of an embodiment can include a closed loop notification, wherein an audit trail can be created to confirm that a particular message or communication has been received by one or more intended recipients.

Other aspects and embodiments of systems, methods, and apparatuses according to the invention are apparent from the following detailed description of the disclosed embodiments and the appended drawings and claims.

DETAILED DESCRIPTION OF EMBODIMENTS

Figure 1:
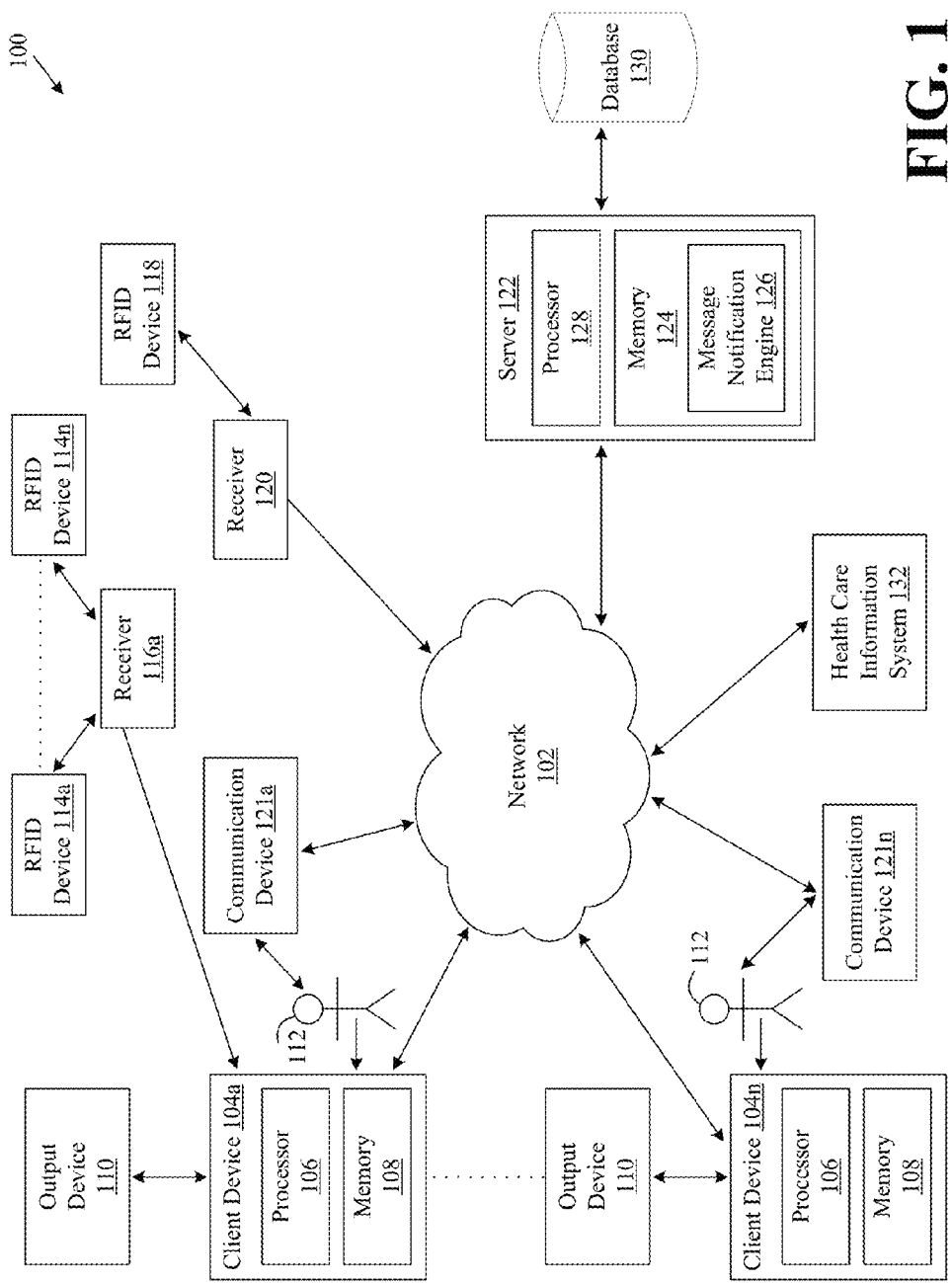
FIG. 1 is an exemplary system in accordance with an embodiment of the invention.

Various embodiments of the invention address some or all of the above issues and combinations thereof. They do so by providing methods, systems, and apparatuses for providing a notification of a message in a health care environment. At least one embodiment can provide a graphical user interface that provides a notification of a message from a source, such as a user or device, or associated with a patient in a health care environment. Message notifications can be displayed on the graphical user interface, and the graphical user interface can be updated in real time when a change occurs to the status of the message from a user or associated with a patient. By providing real time message notification information as well as patient care information in a health care environment, health care personnel can exchange communications, monitor patients, and observe any changes to messages and health care status of patients. Such information can facilitate more immediate and improved responses to the patient's health care needs as well as facilitate improved management and prioritization of health care resources and personnel.

Embodiments of the invention can be implemented to provide communications and notifications of messages or communications between any two entities in a health care environment. Example communications are, for instance, between doctors and nurses; between health care providers (doctors, nurses, etc.) and case managers; to and from environmental services employees, i.e. to request an unscheduled room cleaning; between patients and staff; and between any set of two or more people in the health care environment. Any other communications and notifications of messages or communications between at least two entities can be facilitated by embodiments of the invention.

An "item", as used within this specification, is defined as any area, object, or person in a health care environment, such as a hospital. Examples of an item can include, but are not limited to, a room, an area, a patient, a bed, a gurney, a wheelchair, a walker, a health care worker, or any category or group of items by which such items can be organized.

An "event", as used within this specification, is defined as an activity during any instance or duration of time. Examples of an event can include, but are not limited to, a patient care activity or event, an activity that occurs in a health care environment; an activity capable of being tracked by a health care information system, such as an admission, transfer or discharge of a patient, or the creation of an order or result associated with a patient; completion of an activity or series of activities, an indication by a user via a client device that particular information should be removed, modified or updated; expiration of an item over a period of time; expiration of a preset time; the presence or absence of a patient or staff member in a certain physical area; a patient's falling; a change in the patient location; and an event notification from a patient monitoring device, such as a heart rate monitor.

The term "source", as used within this specification, can include, but is not limited to, a user, a person, an entity, a machine, a device, or any other generator, originator, courier, handler, or transmitter of a message.

A "message", as used within this specification, can include, but is not limited to, a communication, a voice message, an automated message from a machine or a device, a text message, a multi-media message, an e-mail, a voice mail, or any form of communication from one entity to another entity. A message may originate from, and/or be directed to, either a human, a machine, or a device.

A "notification", as used within this specification, can include, but is not limited to, an indicator, text, an icon, a graphical element, a color, timers, animation, sound, or any combination thereof.

"Location information", as used within this specification, can include, but is not limited to, a coordinate, a set of coordinates, a set of geographic coordinates, a set of Cartesian coordinates, a geo-location, a room or area, a floor, a building, a distance from an object, a distance from a person, a position, a location, a position in a room or area, and a position on a floor or building.

An "indicator of care of a patient", as used within this specification, can include, but is not limited to, an order, a request, an approval, an approval of a prescription, a lab result, a safety indicator, a limit, a range, a warning, a statistic, a health status, a date, a time, a timer, contact information, a health-related statistic, a body function, patient care information, a patient care state, a special patient care state, and a patient care activity.

The term "geospatial arrangement", as used within this specification, is defined as the organization of data or information relative to a map or map-type view of a particular area.

Figure 2:
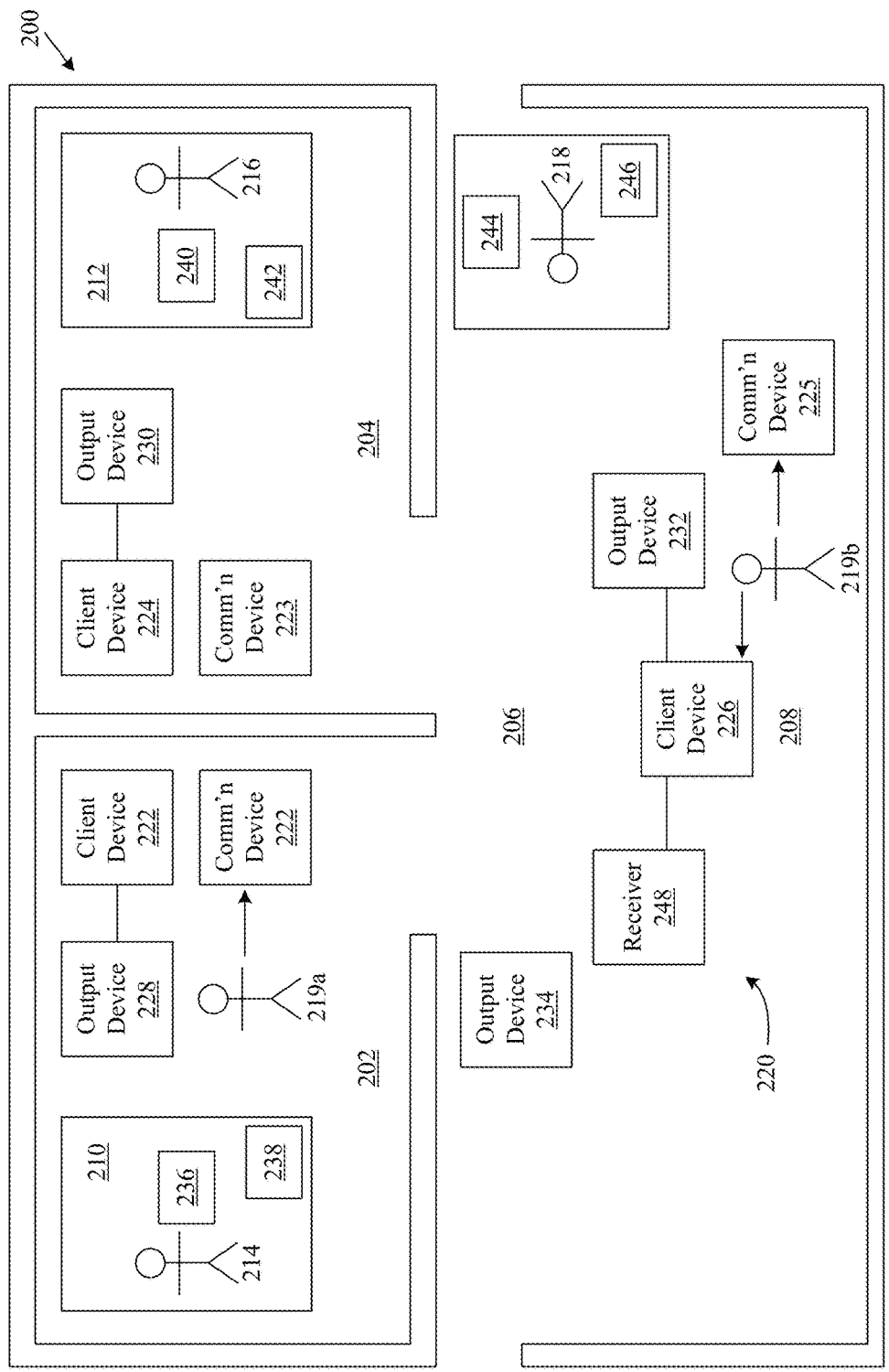
FIG. 2 is an example of an environment in which the system of FIG. 1 can operate in accordance with an embodiment of the invention

FIG. 1 is an exemplary system in accordance with various embodiments of the invention. The system shown is by way of example, and the system can operate in a variety of environments, such as a health care environment or a hospital. One example of a health care environment is shown in FIG. 2. Referring back to FIG. 1, a system 100 is shown with a communications network 102 in communication with at least one client device 104a. Any number of other client devices 104n can also be in communication with the network 102. The communications network 102 shown in FIG. 1 can be a wireless communications network capable of transmitting both voice and data signals. Other types of communications networks can be used in accordance with various embodiments of the invention.

Each client device 104a-n can be a computer or processor-based device capable of communicating with the communications network 102 via a signal, such as a wireless frequency signal or a direct wired communication signal. Each client device, such as 104a, can include a processor 106 and a computer-readable medium, such as a random access memory (RAM) 108, coupled to the processor 106. The processor 106 can execute computer-executable program instructions stored in memory 108. Such processors may comprise a microprocessor, an ASIC, and state machines. Such processors comprise, or may be in communication with, media, for example computer-readable media, which stores instructions that, when executed by the processor, cause the processor to perform the steps described herein. Embodiments of computer-readable media include, but are not limited to, an electronic, optical, magnetic, or other storage or transmission device capable of providing a processor, such as the processor 106, with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any computer-programming language, including, for example, C, C++, C#, Visual Basic, Java, Python, Perl, and JavaScript.

Client devices 104a-n may also comprise a number of external or internal devices such as a mouse, a CD-ROM, DVD, a keyboard, a display, or other input or output devices. As shown in FIG. 1, a client device such as 104a can be in communication with an output device, such as 110. Examples of client devices 104a-n are personal computers, mobile computers, handheld portable computers, digital assistants, personal digital assistants, cellular phones, mobile phones, smart phones, pagers, digital tablets, desktop computers, laptop computers, Internet appliances, and other processor-based devices. In general, a client device, such as 104a, may be any type of processor-based platform that is connected to a network, such as 102, and that interacts with one or more application programs. Client devices 104a-n may operate on any operating system capable of supporting a browser or browser-enabled application, such as Microsoft® Windows® or Linux. The client devices 104a-n shown include, for example, personal computers executing a browser application program such as Microsoft Corporation's Internet Explorer™, Netscape Communication Corporation's Netscape Navigator™, and Apple Computer, Inc.'s Safari™.

A user, such as 112, can interact with a client device, such as 104a, via an input device (not shown) such as a keyboard or a mouse. For example, a user can input information, such as location information associated with a patient, information associated with an indicator of care of a patient, or other information associated with a particular patient, via the client device 104a by keying text via a keyboard or inputting a command via a mouse, or using a stylus or using a bare finger. In another example, a user can input a user query for a patient's care information via the client device 104a by keying text via a keyboard or inputting a command via a mouse. In one embodiment, a user 112 can input one or more commands via a client device 104a to select one or more desired items or other information for display via an output device, such as 110. A user 112 can also input one or more commands via a client device 104a to configure a graphical user interface for an output device, such as selecting a desired geospatial arrangement of items or other information for the graphical user interface.

A user such as 112 can receive output, such as a query response with patient care information or other information associated with a particular patient's information, from an output device, such as 110, via a client device. In one embodiment, information such as location information associated with a patient and a status of care for a patient can be displayed on an output device 110. One suitable output device is a display device capable of displaying information in a geospatial arrangement on a graphical user interface. Another suitable output device is an Awarix™ patient care communication display board capable of displaying location information associated with a patient, an indicator of care of a patient, or other patient process care information in a map, geospatial-type view, table, or grid-type view. Other types of output devices can include, but are not limited to, private-type displays, public-type displays, plasma displays, LCD displays, touch screen devices, and projector displays on cinema-type screens. In some embodiments, the Scalable Vector Graphics ("SVG") standard for describing graphical information, or a similar suitable standard or technique, may be utilized as part of the graphical rendering process. An example of a suitable graphical user interface for an output device is shown and described below in FIG. 3.

In one embodiment, multiple output devices such as public-type displays or flat screen monitors can be mounted in a health care environment, such as in rooms, hallways, on doors, in central monitoring areas, or other areas where users or health care personnel may work, be stationed, or otherwise desire information associated with a patient's location or patient's health care status. In other embodiments, an output device such as private-type display or a computer display monitor can be connected to or associated with a client device, such as a handheld portable computer device or a desktop personal computer (PC).

In the embodiment shown in FIG. 1, a device, such as 114a, capable of providing location information associated with a patient can be in communication with a client, such as 104a. A corresponding receiver, such as 116a, capable of receiving location information associated with a patient can interface or otherwise facilitate communication between the RFID device 114a and the client device 104a. Multiple devices, such as 114a-n, capable of providing location information associated with respective patients can also be in communication with a client, such as 104a, via the same receiver, such as 116a, or any number of other receivers. Other receivers, such as 116n, capable of receiving location information associated with a patient can interface or otherwise facilitate communication between any number of devices capable of providing location information associated with respective patients and a client device. A suitable device capable of providing location information associated with a patient can be a radio frequency identification device (RFID), and a suitable receiver capable of receiving location information associated with a patient can be a RFID reader. Other types of devices and technologies capable of providing location information associated with a patient can be used with other embodiments of the invention, including, but not limited to, passive-type RFID, active-type RFID, wireless, infrared, global positioning satellite (GPS)-type devices or other devices capable of providing location information associated with a patient or otherwise facilitating determination of a location associated with a patient, staff member, or piece of medical equipment.

In at least one embodiment, a device capable of providing location information associated with a patient, and a corresponding receiver capable of receiving location information associated with a patient can communicate with a client via a network. For example as shown in FIG. 1, RFID device 118 and receiver 120 can communicate with client device 104a via the network 102. In another embodiment, a device capable of providing location information associated with a patient can communicate with both the network 102 and one or more client devices 104a-n, either with or without a corresponding receiver capable of receiving location information associated with a patient. In some instances, a receiver capable of receiving location information associated with a patient can be incorporated into or otherwise associated with a client or another device associated with a network. In any of these instances, a device capable of providing location information associated with a patient and a corresponding receiver capable of receiving location information associated with a patient can communicate the location information to a remote location via a network, such as 102.

In one embodiment, any type of wireless location tracking technology, such as active RFID, can be used to provide real time location information about one or more patients' locations in a health care environment. Such locations can be tracked automatically by a message notification engine, such as 126 in FIG. 1 and described below, via the wireless location tracking technology as each patient moves throughout a health care environment, such as a hospital, floor, or room.

In one embodiment, each client device, such as 104a-n, can be associated with a unique identifier. Examples of suitable identifiers are serial numbers, Ethernet MAC addresses, IP addresses, numbers generated via random and/or pseudo-random algorithms etc. A database, such as 130 in FIG. 1 and described below, or other data storage device can store the unique identifiers for subsequent retrieval. In this manner, the system 100 can record the location of a client device, such as 104a or a desktop computer, so that the display configuration for an associated output device, such as 110, can be changed based on the location of the client device or desktop computer. For example, a client device or desktop computer on a third floor of a building in a health care environment may only be able to display information about patients on that particular floor. By associating a unique identifier with each client device or desktop computer, the system 100 can track the location of each client device or desktop computer, and in particular, mobile client devices, to support dynamic information display on the associated output device based on the current location of the particular client device.

A user such as 112 can also interact with a communication device, such as 121a. Each of the communication devices 121a-n can interact with a network, such as 102. In one embodiment, a communication device can interact with a public switched telephone network or the Internet. A communication device can include, but is not limited to, a telephone, a smartphone, a cellular telephone, a mobile phone, a satellite phone, a wireless phone, an e-mail device, and a messaging device. For example, a user can dial a particular phone number or extension via a communication device, such as 121a. Using a voice and/or data channel via a network, such as 102, the user 112 can enter information, such as keypad numbers, text, a voice input, or a voice message, and transmit the information via the communication device 121a.

The system 100 can also include a server 122 in communication with the network 102. In one embodiment, the server 122 can be in communication with a public switched telephone network or the Internet. The server 122 shown can include memory 124, and a message notification application program, also known as a message notification engine 126. The server 122 can transmit and receive information to and from multiple sources via the network 102, including a communication device such as 121*a*, a client device such as 104*a*, a database such as 130 or other data storage devices, and a health care information system such as 132.

In one embodiment, a message notification engine 126 can receive information from a communication device, such as 121*a*, including keypad numbers, text, a voice input, an automated message from a machine or device, or a voice message from a communication device. A suitable message notification engine can include interactive voice response (IVR)-type functionality, instructions, or methods. In addition, a suitable message notification engine can include voice mail or messaging-type functionality, e-mail, instructions, or methods. In at least one embodiment, a suitable message notification engine can also include voice or speech recognition-type functionality, e-mail, instructions, or methods. For example, a user such as 112 can utilize a communication device 121*a* to interact with a message notification engine 126 via network 102. The message notification engine 126 can provide interactive voice response-type functionality to prompt the user 112 to select commands or enter text via a keypad (not shown) associated with the communication device 121*a*. Upon receipt of one or more commands or text from the communication device 121*a*, the message notification engine 126 can provide voice mail-type functionality to permit the user 112 to enter a voice message or one or more voice commands. The message notification engine 126 can store the voice message in memory 124, a database 130 or other data storage device, such as a voice mail box, for subsequent retrieval.

In another example, a message notification engine 126 can provide interactive voice response-type functionality to prompt the user 112 to select commands or enter texts via a keypad (not shown) associated with the communication device 121*a*. Upon receipt of one or more commands or text from the communication device 121*a*, the message notification engine 126 can provide voice mail-type functionality to permit the user 112 to receive a voice message or other information. The message notification engine 126 can retrieve a previously stored voice message or other information from memory 124, a database 130 or other data storage device, such as a voice mail box.

In one embodiment, a message notification engine 126 can provide a variety of different interactive voice response-type or voice mail-type prompts and menus depending on the skill level of a user, such as 112. For example, prompts and menus can be provided for some or all of three different skill levels, e.g., beginner, intermediate, and expert. In another example, a user can predefine or select a particular level for when he or she interacts with the message notification engine 126.

In yet another embodiment, a message notification engine 126 is capable of providing a user the capability to retrieve or otherwise receive a previously stored message or other information directly from an output device or display screen, such as 110, associated with a client device or computer, such as 104*a*, rather than having to dial an access number, telephone number or extension. For example, when a message is available for a particular user, a notification can be displayed on an output device such as 110. The notification can be formatted as a particular shaped icon, such as one or more letters, i.e. "ED", with a predefined meaning for the user, such as "report ready from the emergency department (ED)," described below as 301 in FIG. 3. When the user views the icon on the output device, the user can recognize the icon and associated meaning of the icon, and thus, retrieve or otherwise receive the message without having to dial or call. For example, the user can retrieve a message via a client device, such as 104*a*, or computer.

In another embodiment, a message notification engine 126 is capable of providing a user the capability to transmit a message and to access a previously stored message or other information from any conventional telephone or communication device. For example, a message notification engine 126 can receive a text message from a text communication device, such as a pager, text messaging, or e-mail communication device. The message notification engine 126 can convert a text message to a voice message using a text-to-speech conversion application, method, or routine. The voice message can be stored for retrieval by a recipient using any voice communication device, such as a telephone, mobile phone, or the like. Alternatively, a voice message from a voice communication device, such as a telephone or mobile phone can be received by a message notification engine 126. The message notification engine 126 can convert the voice message to a text message using a speech-to-text conversion application, method, or routine. The text message can be stored for retrieval by a recipient using any text communication device, such as a pager, text messaging, or e-mail communication device.

In yet another embodiment, a message notification engine 126 can provide a user with the capability to reply to a received message with an additional, new message to the sender of the original message. For example, once a user, such as 112, receives a previously stored message or communication from the message notification engine 126, the message notification engine 126 can prompt the user 112 to reply to the sender of the previously stored message or communication. If desired, the user 112 can leave and store a voice message or other communication with the message notification engine 126 for delivery back to the original sender. The message notification engine 126 can provide a notification via an output device, such as 110, that a message is available for the original sender. When the original sender interacts with the message notification engine 126, the original sender can receive the newly stored voice message or communication from the user 112, and the output device 110 can be updated accordingly. Any number of iterations of the process described above can result in multiple exchanges of messages between the original sender and user 112, and the output device 110 can be updated as needed.

In still another embodiment, a message notification engine 126 can provide the capability to increase or decrease the relative urgency of any message, such as a previously stored message or communication. For example, a user 112 can interact with a message notification engine 126 to prioritize, designate, or otherwise modify the relative urgency of a previously recorded and stored message or other communication. This may be particularly necessary in the event the message has yet to be received by a recipient, or if the relative urgency of the message has increased or decreased. In some instances, the user 112 may be prompted to redirect the stored message or communication for transmission via a different communication mode, such as sending the message via a page, a normal voice mail, or an e-mail. In such instances, the message notification engine 126 can interact with any number of communication technologies and, if necessary, convert the message from speech to text, or vice-versa, for transmission or delivery via a desired communication mode.

In addition, a message notification engine 126 can provide location information and indicators of care for any number of patients in a health care environment. In one embodiment, a message notification engine 126 can receive location information associated with a patient from a device capable of providing location information associated with a patient, such as 114a or an RFID. The message notification engine 126 can correlate the location information with any other information, such as an indicator of care of a particular patient, and cause the display of information on one or more output devices, such as 110.

Messages or other communications for a user or associated with a patient can be received by the server 122 via the network 102 from one or more client devices 104a-n, memory 124, the database 130 or other data storage devices, from other information systems, and from a health care information systems 132. For example, a message from a user 112 or any other source, human or machine, can be stored by the message notification engine 126 in the database for subsequent retrieval. In other embodiments, a message notification engine such as 126 can record and document some or all messages and communications delivered to users, or any device associated with a user. In this manner, messaging and communications traffic facilitated by a message notification engine, such as 126, or system 100, can be audited or analyzed for training purposes.

Information associated with various indicators of care of multiple patients can be also received by the server 122 via the network 102 from one or more client devices 104a-n, memory 124, the database 130 or other data storage devices, from other information systems, and from health care information systems, such as an admission, discharge, and transfer (ADT)-type system. In one embodiment, information associated with an indicator of care of a patient can be input by a user 112, such as an attending physician, via a client device 104a, such as a handheld portable computer or desktop computer. The information can be received by the server 122 via the network 102 for processing by the message notification engine 126 or storage by the database 130 or other data storage device. In another embodiment, information associated with an indicator of care of a patient can be received or otherwise obtained from a health care information system 132, database 130, or other data storage device or information source. The message notification engine 126 can receive or obtain such information from such sources via the server 122 and the network 102.

The message notification engine 126 can also permit a user, such as 112, to transmit a query for patient care information. For example, the message notification engine 126 can provide functionality via a client device, such as 104a, to allow a user 112 to transmit a query to obtain information associated with a particular patient. The message notification engine 126 can receive and process the query to generate a query response, for instance, a location associated with the patient and an indicator of care of the patient.

The message notification engine 126 is further capable of facilitating a geospatial arrangement and graphical display of information associated with a particular patient on an output device such as 110, for example, a notification of a message for a particular user or associated with a particular patient. In addition, the message notification engine 126 can facilitate the geospatial arrangement and graphical display of location information associated with the patient and an indicator of care of the patient.

In one embodiment, the message notification engine 126 can facilitate a display of graphical information on a graphical user interface in a geospatial arrangement on an output device, such as 110. The message notification engine 126 can also facilitate the generation of graphical representations of information on a graphical user interface for an output device including text, icons, graphical elements, colors, timers, animation, or any combination thereof. For example, an icon indicating a notification of a message for a particular user or associated with a particular patient can be displayed adjacent to a user's name or patient's room on a graphical user interface.

When new or changed information is received by the message notification engine 126, such as receipt of a message, or delivery of a message, the message notification engine 126 is capable of updating the information on a graphical user interface for the output device in real time by displaying some or all of the new or changed information. Likewise, message notification engine 126 is capable of updating the information on a graphical user interface using information from a device capable of providing location information associated with a patient or a user input of an indicator of care of a patient.

In addition, the message notification engine 126 is capable of displaying any number of items in a particular health care environment, and formatting the items in any type of view provided on a graphical user interface for an output device, such as a map, geospatial-type view, table, or grid-type view. In this manner, a user can obtain and monitor the receipt and delivery of messages as well as selected patient care information in a geospatial arrangement on a graphical user interface for an output device, and view any new or changes to the information on the graphical user interface as they occur.

Similar to the client devices 104a-n, the server device 122 shown comprises a processor 128 coupled to a computer-readable memory 124. The server device 122 can be in communication with a database, such as 130, or other data storage device. The database 130 can receive and store data from the server 122, or from a client device, such as 104a, via the network 102. Data stored in the database 130 can be retrieved by the server 122 or client devices 104a-n as needed.

In one embodiment, a server 122 and the message notification engine 126 can receive a message or other communications from a user 112. The server 122 and the message notification engine 126 can also receive location information associated with a patient, information associated with an indicator of care of a patient, or other patient care information. The message notification engine 126 can store some or all of the information in memory 124, the database 130 or other data storage device for subsequent retrieval.

Server device 122, depicted as a single computer system, may be implemented as a network of computer processors. Examples of a server device 122 are servers, mainframe computers, networked computers, a processor-based device, and similar types of systems and devices. Client processor 106 and the server processor 128 can be any of a number of computer processors, such as processors from Intel Corporation of Santa Clara, Calif. and Motorola Corporation of Schaumburg, Ill. The computational tasks associated with rendering the graphical image could be performed on the server device(s) and/or some or all of the client device(s).

The server device 122 can integrate with and communicate with any number of communication systems to transmit and receive voice or data communications in a health care environment. In one embodiment, a server device can communicate with a public switched telephone network and the network 102 shown in FIG. 1. In another embodiment, a server device can communicate with any number of wireless data and voice networks to transmit and receive voice or data communications in a health care environment.

The server device 122 can integrate with and can communicate with other information systems in a health care environment to receive information, such as real time events associated with one or more patient care processes, and indicators of care of one or more patients. Such real time events and indicators can be stored in the query support database 130 or other data storage device to support real time and dynamic updating of information displayed on some or all of the output devices 110. As shown in FIG. 1, an information system such as a health care information system 132 can communicate with the server 122 via the network 102. In one embodiment, integration of the server 122 with other suitable information systems can be based on an industry standard HL7 communication model. In another embodiment, a custom integration of the server 122 with other suitable information systems can achieve similar results to an industry standard HL7 communication model. Examples of suitable information systems, the server device 122 and other components of the system 100 can integrate with or otherwise communicate with, can include, but are not limited to, an ADT-type (admission, discharge, and transfer) system, ordering systems, result reporting systems, lab-type systems, pharmacy-type systems, radiology-type systems, transcription-type systems, environmental services-type systems, and transportation-type systems.

FIG. 2 illustrates an example of an environment in which a system according to an embodiment of the invention can operate. By way of example, the system 100 in FIG. 1 can operate in the environment 200 shown. The environment 200 shown in FIG. 2 is a health care environment, such as a hospital or an assisted care facility. The environment 200 shown in FIG. 2 is by way of example, and illustrates a portion of a hospital or assisted care facility. The environment 200 shown includes multiple rooms 202, 204, 206, 208 or areas, and beds 210, 212 in some of the rooms 202, 204. Any number of patients, such as 214, 216, 218, can be within the environment 200 at any particular time. Two rooms 202, 204 shown adjacent to each other can be patient care rooms with a respective bed 210, 212 for each patient 214, 216 shown. In other embodiments, rooms may be on different floors or in different areas of a health care environment. A hallway or corridor 206 adjacent to rooms 202, 204 is also shown, with another patient 218 in the corridor 206. A monitoring area 208 can be adjacent to the corridor 206 and rooms 202, 204. A first user 219a or health care worker is shown in one room 202, and a second user 219b or health care worker is shown in the monitoring area 208. Embodiments of the invention can operate with any other configuration of users, rooms, corridors, central monitoring or orderly areas, or other rooms in a health care environment.

The system 220 shown in FIG. 2 can operate similar to the system 100 shown and described in FIG. 1. The system 220 can include some or all of the system components shown in FIG. 1. In some instances, some or all of the components of the system 220 may be within the environment 200, and in other instances, some components of the system 220 may be outside of the environment 200. For example, system components not shown in FIG. 2 but which can be part of the system 220 can include a network, a server, and a message notification engine, similar to like components described in FIG. 1.

The system 220 shown in FIG. 2 can also include client devices 222, 224, 226, communication devices 221, 223, 225, associated output devices 228, 230, 232, 234, a series of devices 236, 238, 240, 242, 244, 246 capable of providing location information associated with a patient, and a receiver device 248 capable of receiving location information associated with a patient. The components of system 220 described above can operate in a similar manner to the like components described in FIG. 1.

In the embodiment shown in FIG. 2, a first user, such as 219a can transmit a message from a communication device, such as 221. The system 220 can receive and store the message, and facilitate the display of a notification on some or all of the output devices 228, 230, 232, 234. A second user, such as 219b, can view the notification on an output device, such as 234, and retrieve the stored message from the system 220 via another communication device, such as 225. Users 219a, 219b can utilize any communication device 221, 223, 225 or output device 228, 230, 232, 234 to receive a notification, and to transmit, store, and receive a message. In one embodiment, one or more client devices 222, 224, 226 can be utilized with an output device 228, 230, 232, 234 to receive a notification, and to transmit, store, and receive a message. In this manner, a user can transmit a message for subsequent retrieval, and a recipient user can be notified of the message and can retrieve the message when needed.

Furthermore, in the embodiment shown in FIG. 2, a patient can be associated with a device capable of providing location information associated with a patient by mounting a RFID tag or another type of location information type device to a chart associated with the patient. In some instances, a patient chart can accompany a patient as the patient moves within a health care environment, such as a hospital. A device capable of providing location information associated with a patient, such as a RFID tag, can be mounted to a patient chart associated with the particular patient. A device capable of providing location information associated with a patient can be mounted to other types of charts, documents, or other media associated with a particular patient in accordance with embodiments of the invention. In this manner, as a patient moves through a health care environment with an associated patient chart, the general location of the patient can be monitored by a message notification engine, such as 126, via a receiver capable of receiving location information associated with the patient. The message notification engine 126 can facilitate the graphical display of such information in a geospatial arrangement via a graphical user interface, such as 300, for an output device, such as 110. In one embodiment, a message notification engine 126 can communicate with other information systems, such as an admissions, discharge, and transfer (ADT)-type system, to automatically receive new or modified patient bed assignment information when a new patient is admitted to or enters a health care environment, or when a patient is transferred from or discharged from a health care environment. The message notification engine 126 can incorporate and display information received from other types of information systems with previously received location information associated with a patient and indicators of care of the patient.

In another embodiment, a patient can be associated with a device capable of providing location information associated with a patient by mounting a RFID tag or other location information type device to the patient. This can be accomplished by use of a wearable tag, band, chip, adhesive, implant, stamp, or other device or technique. A RFID or tag number can then be associated with the patient, and a message notification engine, such as 126, can track the RFID, tag number, and patient associated with the RFID, tag, and tag number as the patient moves within a health care environment.

In yet another embodiment, a bed can be associated with a device capable of providing location information associated with a patient by mounting a RFID tag or other location information type device to the bed. When a patient is assigned a particular bed, the patient is associated with the bed, and therefore associated with the device mounted to the bed. The association between a bed and a patient, also known as a patient bed assignment, can be tracked and managed using the system 100. In some instances, similar information can be received by a message notification engine, such as 126, via an automated information system, such as an admission, discharge, transfer (ADT)-type system. In any instance, the system 100 via the message notification engine 126 can incorporate and display information received from ADT-type systems and other similar systems, devices or techniques that track and manage patient bed assignment information. In this manner, a patient who is associated with a tag can be tracked using patient admission, transfer, and discharge information from ADT-type systems, and the system 100 can graphically display such information in a geospatial arrangement via a graphical user interface, such as 300, for an output device, such as 110.

As shown in FIG. 2, a client device 222, 224, 226 and associated output devices 228, 230, 232, 234, can be located in or adjacent to each room 202, 204, in a hallway or corridor, and in a remote or adjacent monitoring area 208. In other embodiments, an output device such as a display screen can be located on a door, wall, floor, ceiling, furniture, or other objects associated with a room or located in a room. In any instance, a user, such as 219a, can receive graphical information in a geospatial arrangement via a graphical user interface for an output device, such as 228, 230, 232, 234, including a notification of a message for a user or associated with a patient. Other information can be received via an output device, including location information associated with a patient, an indicator of care of a patient, and other patient care information. A user 219a can also interact with a client device, such as 226, to enter or transmit a message, or alternatively, to retrieve a message for a user or associated with a patient. In addition, a user can also interact with a client device to input information associated with a patient, such as an indicator of care of a patient, or to submit a query or other request for information associated with a particular patient. Similar to the system 100 in FIG. 1, the system 200 in FIG. 2 can provide a notification of a message for a user or associated with a patient. Similarly, the system 200 in FIG. 2 can also provide a query response to the user's query, such as displaying graphical information in a geospatial arrangement via a graphical user interface for an output device, such as 232.

Figure 3:
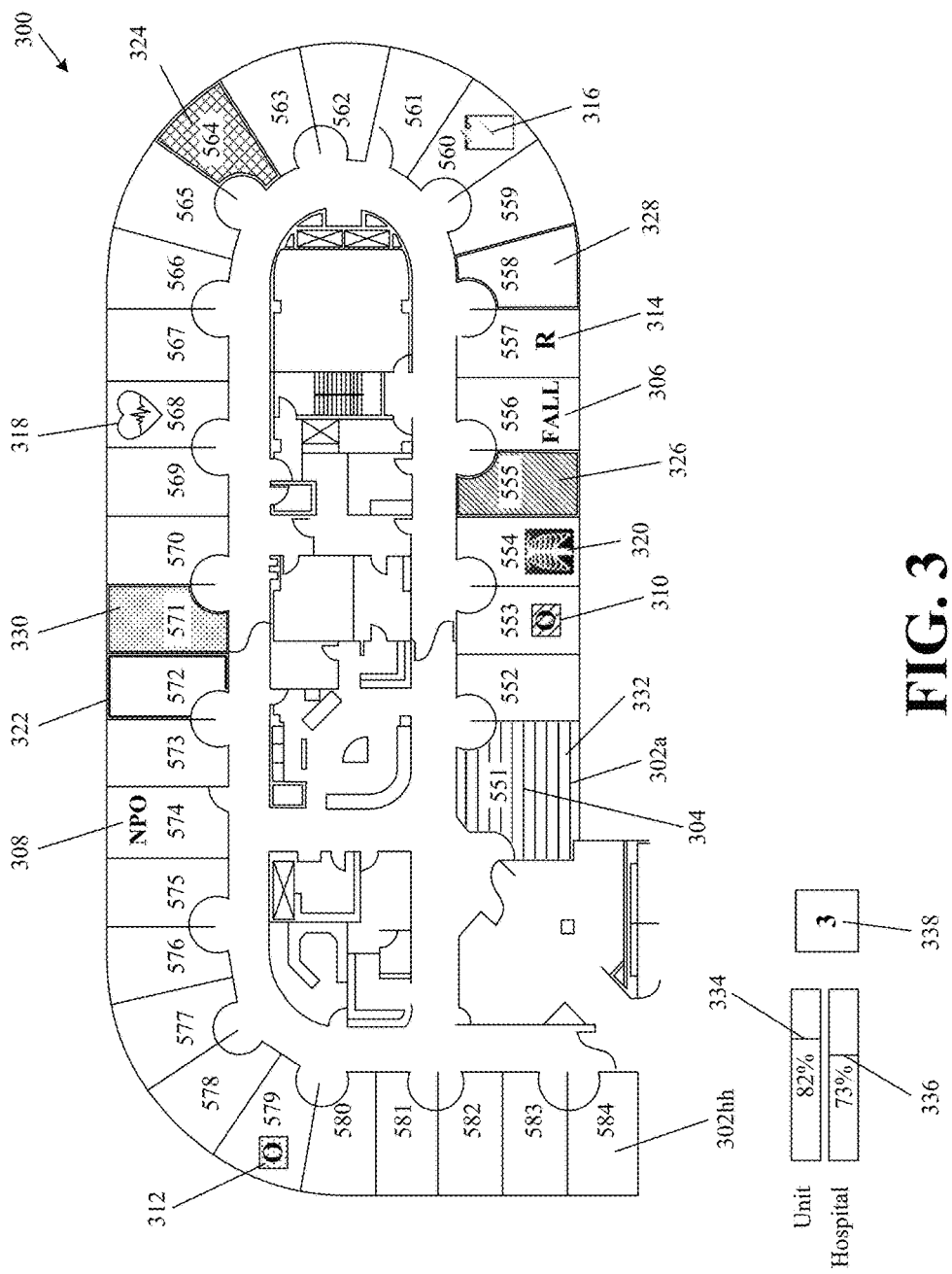
FIG. 3 illustrates an exemplary graphical user interface for the system of FIG. 1 in accordance with an embodiment of the invention.

In FIG. 3, an example of a graphical user interface 300 for an output device is shown. In the embodiment shown, an output device such as a display monitor can facilitate display of the graphical user interface 300 shown. The graphical user interface 300 can provide a geospatial arrangement of various information, such as graphical information, associated with a patient, including a notification of a message for a particular user or associated with a patient. In addition, information such as location information associated with a patient, and an indicator of care of a patient can be provided. For example, the graphical user interface can include a map or geospatial view of a health care environment, such as a hospital. A map or geospatial view can be divided, for example, into multiple areas that represent the relative location of rooms in a hospital. One or more areas within or adjacent to the map or geospatial view can display graphical information associated with a notification of a message for a particular user or associated with a patient. Other graphical information can be displayed including a status of a particular patient, such as location information associated with a patient or an indicator of care of a patient. Such areas within the map or adjacent to the map can include other graphical information including, but not limited to, text, icons, graphical elements, colors, timers, animation, or any combination thereof.

In one embodiment, one or more messages associated with a particular user or patient can be displayed within or adjacent to the representation of a room on a graphical user interface. For example, an icon indicating the receipt of a message for a user or associated with a patient can be displayed in a graphical user interface, such as 300, adjacent to a corresponding room or area associated with the user or patient. In the example graphical user interface 300 shown in FIG. 3, a notification indicating receipt of a message, such as an icon 301 with one or more letters, i.e. "ED", or text with the words "report ready", can be displayed within a map or geospatial view of a healthcare environment. Other types of notifications and indicators of a notification can be displayed in a graphical user interface in accordance with embodiments of the invention.

In another embodiment, one or more items associated with a particular room can be displayed within or adjacent to a representation of the room on a graphical user interface. For example, items such as beds, patients, health care personnel, instruments, tools, gurneys, wheelchairs, walkers, and other objects or persons in a health care environment can be displayed in a graphical user interface, such as 300. In this embodiment, an association between each item and a respective device capable of providing location information can be made by mounting a RFID tag or other location information type device to the item. Location information associated with a particular item can then be received by a message notification engine, such as 126, and a representation of each item can be displayed via a graphical user interface for an output device. In this manner, various items can be displayed in a geospatial arrangement by a message notification engine via a graphical user interface for an output device. This permits the graphical user interface to convey various amounts of graphical information about a particular activity for a particular patient. Items can be graphically represented by any combination of text, icons, graphical elements, colors, timers, animation, or any combination thereof.

In the embodiment shown in FIG. 3, location information associated with a patient can be displayed by the graphical user interface 300. Using either of the systems 100, 220 described above, or a system in accordance with an embodiment of the invention, a graphical user interface 300 can receive and display location information associated with a particular patient. As discussed above with respect to systems 100, 220, wireless location tracking technologies such as active RFID can allow one or more patients' locations to be tracked automatically as they move throughout a health care environment. For example, for a particular patient bed, such as 210 in FIG. 2, or room, such as 202, a graphical user interface 300 can display a patient location as, for instance, an icon or other graphical representation over the particular bed or room to permit a user to view a current patient location on the graphical user interface 300.

In the example, graphical user interface 300 shown, consecutively numbered patient rooms 302a-302hh, in a counterclockwise orientation, on a particular floor of a hospital can be displayed within the map or geospatial view. Other rooms or areas in the map or geospatial view may not have a corresponding room number, and a respective room number may not be displayed for such rooms or areas, such as a corridor, hallway or monitoring area. A representation of rooms for a building, floor, or environment may be a relatively simple layout or general floor plan, and does not need to be to scale or depict an actual aspect ratio, door location, or orientation of the actual room, floor, building, or environment. Any layout, format, or representation of rooms in relation to each other can be used for a map or geospatial view of an environment, and may change based on some or all of the following: a user, user's role, location, time, date, or patient care event.

Text 304 for corresponding room numbers, such as "551" through "584", can be displayed relative to the respective patient rooms 302a-302hh. Other text can be displayed relative to a room, for instance, a patient safety indicator or a physician name. In one example, text with a patient safety indicator, such as the term "FALL" 306 or "NPO" 308, can indicate a heightened risk of falling or nothing by mouth, respectively, for a patient in a particular room. In another embodiment, any text can be used to represent various rooms, patient safety indicators, physician names, patient care states, activities, or other indicators of care of a patient.

Other graphical information such as an icon can be displayed within or adjacent to a room on a graphical user interface, such as 300. An icon can represent, for example, a patient care state or activity such as a new order, a patient location, or a step in a patient care process. By way of example, an "O"-shaped icon of a first color 310, such as blue, can be displayed within or adjacent to a particular room to indicate a patient with an unfulfilled order having normal urgency. In another example, an "O"-shaped icon of a second color 312, such as red, can be displayed within or adjacent to a particular room to indicate a patient with an unfulfilled order having high ("stat") urgency. Examples of a patient care state can include, but are not limited to, inpatient, outpatient, ready for discharge, ready for transfer, and whether a patient's room is under isolation to avoid infection, scheduled or expected discharge time. Examples of a patient care activity can include, but are not limited to, whether a newly arrived patient has been seen by a nurse yet.

In another example, a "R"-shaped icon 314 can be displayed within or adjacent to a particular room to indicate that a new laboratory result associated with the patient is available, which may or may not be displayed by the graphical user interface. By way of another example, a "clipboard and thermometer" icon 316 can be displayed within or adjacent to a particular room to indicate a respective patient who has not had their vital signs recently taken or measured. In yet another example, a heart-shaped icon 318 can be displayed within or adjacent to a particular room to indicate a patient is in a cardiology lab or department. In another example, a "x-ray" icon 320 can be displayed within or adjacent to a particular room to indicate a respective patient is in a radiology lab or department. In another embodiment, any combination of icons can be used to represent various patient care states, activities, or other indicators of care of a patient.

Graphical information such as graphical elements can be displayed within or adjacent to a room on a graphical user interface, such as 300. A graphical element can represent, for example, a special patient care state such as a patient on isolation. For example, a graphical element can be an outline 322 highlighting some or all of a particular room to indicate a special care state of a patient in the room. In another embodiment, any combination of graphical elements can be used to represent various patient care states or other indicators of care of a patient.

Graphical information such as colors can be displayed within or adjacent to a room on a graphical user interface, such as 300. A color can represent, for example, a particular patient care state, such as an inpatient or observation patient, or a representation of a room state, such as an unoccupied room or an unclean room. By way of example, a room shaded a first color 324 such as green can indicate a patient in a particular room is an inpatient. In another example, a room shaded with a second color 326 such as blue can indicate a patient in a particular room is under observation or an observation patient. In yet another example, a room without any color shading 328 can indicate an unoccupied room. In still another example, a room shaded with a third color 330 such as brown can indicate a room that is unclean. Yet another color, such as yellow, can indicate that the patient is scheduled for discharge. In another embodiment, any combination of colors can be used to represent various patient care states or other indicators of care of a patient.

Graphical information such as timers can be displayed within or adjacent to a room on a graphical user interface, such as 300. One or more timers can be associated with a notification of a message for a user or associated with a patient, and can be incorporated in an icon, such as 301 in FIG. 3, or other type of graphical element or feature. A timer can indicate an age of a message or notification. For example, on a graphical user interface, a timer can be displayed in a geospatial arrangement adjacent to an icon representing a notification for a message or a user or associated with a patient. The displayed timer may continue to run and be continuously updated in real time until the message or communication is retrieved or otherwise received by a recipient.

In another embodiment, a timer can also represent, for example, a starting time, an ending time, or both, for a particular patient care event. In another example, a timer can indicate how long a patient in a particular room has been in observation. In one embodiment, a timer can be displayed adjacent to or within a room or other area displayed on a graphical user interface, such as 300, to represent a duration of time that a patient has been in a particular room or area. In this manner, a user can monitor a patient's location as well as the duration of the patient's movement in particular rooms or areas, thus saving time for health care personnel and improving patient safety.

Graphical information such as animation can be displayed within or adjacent to a room on a graphical user interface, such as 300. Animation can include, for example, any movement, rotation, flashing, fading, cycling, or any combination of activity by graphical information thereof. Such animation can be utilized by a message notification engine, such as 126, with the display of a notification of a message for a user or associated with a patient. For example, the color of an icon associated with a notification of a message for a user or associated with a patient can be frequently changed or the icon can appear as a flashing icon on a graphical user interface. In either or both of these instances, the use of such effects can indicate a relatively higher urgency level for a particular message. Likewise, cessation of such effects can indicate a relatively lower urgency level for a particular message.

By way of another example, animation such as an alternating green-colored line pattern 332 can represent a patient for whom a doctor has written a discharge order.

Other types of graphical representations or techniques can be used to represent an item and convey graphical information about a particular activity for a particular patient in a graphical user interface, such as 300, for an output device, map, or other geospatial view in accordance with embodiments of the invention.

In the lower portion of the graphical user interface 300, one or more graphical indicators, such as capacity indicators 334, 336, 338, can be displayed. A capacity indicator can represent any characteristic of the health care environment to accommodate additional patients. For example, one capacity indicator can be a bar graph 334 indicating a unit capacity, such as 82%. Unit capacity can be a representation of the capacity of a particular group within a health care environment, such as a building floor or patient care group, and the ability of the particular group to accommodate additional patients. In another example, a capacity indicator can be another bar graph 336 indicating hospital capacity, such as 73%. Hospital capacity can be a representation of the capacity of a particular health care environment, such as a hospital or assisted care facility, and the ability of the particular health care environment to accommodate additional patients. By way of example, a capacity indicator can be a numeric FIG. 338, such as "3", indicating a critical shortage of some type of bed or the criticality of capacity utilization in a health care environment.

In the embodiment shown in FIG. 3, the map, geospatial view, and other display areas of the graphical user interface 300 can be dynamically updated in real time by a message notification engine, such as 126 in FIG. 1, as new or updated information is determined, received, or otherwise detected, such as when a message is retrieved by a user, when new or additional messages for a user or associated with a patient are received, or when the relative urgency of a message is increased or decreased. For example, a notification of a message for a user or associated with a patient can be updated or removed from a graphical user interface upon receipt of the message by a recipient. In another example, a notification of a message for a user or associated with a patient can be automatically removed from a graphical user interface if the message is not retrieved or otherwise received in a predefined amount of time.

In one embodiment, a graphical user interface 300 can be dynamically updated in real time when a patient care event occurs. Examples of patient care events can include, but are not limited to, a new order associated with a patient, a new order for medicine or a medical procedure or measurement, results from a lab or department, a prescription approval, a new or updated patient location, a new or updated patient care status, a new physician or health care person assignment, and a new or updated contact for a patient.

In one example, a patient care event can be a new order placed by, or on the behalf of, a particular patient. If, for instance, a user desires to create a new order for a patient, a user, such as 112 in FIG. 1, new order information can be transmitted from a client device, such as 104a, to a message notification engine, such as 126. The message notification engine 126 can generate and facilitate a display of graphical information via a graphical user interface for an output device, such as displaying an "order" icon or "O", on the graphical user interface, such as 310. The order icon can be positioned on the graphical user interface 300, relative to a pre-existing graphical representation of a location where the particular patient is, such as a room or bed on a map or other geospatial-type view. When a user, such as 112, views the graphical user interface 300, the order icon 310 can notify or otherwise inform the user or other health care personnel about the existence of the user's new order for the patient.

Often times multiple patient care events can occur simultaneously or in overlapping durations of time. In one embodiment, a graphical user interface for an output device can facilitate the display of multiple, simultaneous pieces of information. In one instance, multiple display areas can be defined within a single item, such as a room. Each display area within the particular item can display various types and amounts of information, such as orders, or patient safety information. In this manner, various types and amounts of information, such as text, an icon, and timers, can be displayed with respect to a particular item, such as a room.

In another embodiment, if a particular display area for a single item, such as a room, has multiple pieces of information to display, the multiple pieces of information can be sequenced in a predefined manner. For example, if the multiple pieces of information exist, each piece of information can be rotated through the display area relatively quickly, thus permitting a user to view some or all relevant patient information in the display area. The time each piece of information is displayed in a particular display area can be configurable or predefined by a user or via a message notification engine, such as for two to three seconds.

In another example, multiple orders for a patient can be displayed by corresponding order icons positioned adjacent to a representation of a patient's location, such a room. In another example, a status of results from one or more laboratories or departments, such as radiology, can be displayed by corresponding order icons positioned adjacent to a representation of a patient's location, such a room. Other examples of patient care events can include, but are not limited to, approval of a pharmacy prescription, a new or existing patient location, a patient safety indicator such as a risk (fall, NPO) or medical condition (deaf), a patient status timer, a physician name, a nurse name, a care provider name, contact information, and a request for communication with others. Some or all types of patient care events can be simultaneously displayed via a graphical user interface, such as 300, for an output device in a map, or other geospatial view.

In another embodiment, information associated with each item displayed on a graphical user interface can change over time, and new or changed information can automatically be added or updated via a graphical user interface in real time or as information is received. For example, a doctor can write a new order for a patient in a particular room. When the doctor or other health care personnel transmits via a client device, such as 104a, the order information to a message notification engine, such as 126, the message notification engine can facilitate display of a corresponding graphical representation of the order information via a graphical user interface for an output device. In this instance, the patient care event of writing a new order can result in an "order" icon being displayed over the room displayed by the graphical user interface, such as an "O" icon 310 displayed over a graphical representation of the particular room on a map. Likewise, if the doctor cancels or modifies the new order for the patient in the particular room, the doctor or other health care personnel transmits the canceled or modified order information to the message notification engine, and the message notification engine 126 can facilitate display of a corresponding graphical representation of the canceled or modified order information via the graphical user interface for an output device. In this instance, the patient care event of canceling or modifying an order can result in an "order" icon being removed from the display of the room shown via the graphical user interface, such as an "O" icon 310 removed from a graphical representation of the particular room on a map.

Embodiments of the invention can process various types of user queries for information in a health care environment, and can also display various types of formatted or unformatted responses to queries in a graphical user interface for an output device. The examples and embodiments provided herein are by way of example and are not intended to be limiting.

In one embodiment, a user, such as 112, can utilize a client device, such as 104a, to generate and transmit a query for selected information to a message notification engine 126, database 130, or other data storage device. In response to the user's query, the message notification engine, database, or other data storage device can process the query to generate and return a query response. The message notification engine can determine information in response to the query, and transmit the information and query response to the client device utilized by the user. The message notification engine 126 can also facilitate a display of graphical information in a geospatial arrangement based at least in part on the query response on an output device associated with the client. For example, a user can transmit a query for a particular patient's information to a message notification engine such as 126. In response to the user's query, the message notification engine 126 can determine a response to the query, and if needed, can communicate with a database, such as 130, or other data storage device to obtain requested patient information in response to the query. The message notification engine 126 can return selected information, i.e. patient information, to the user via the client device 104a in response to the user query. The message notification engine 126 can also facilitate the display of a graphical representation of some or all of the patient information via a graphical user interface, such as 300, for an output device, such as 110.

In another example, a subset of items may be of particular interest to a user based on a user's particular role, location, or other context-type criteria. The user can generate and transmit a predefined query or set of instructions based in part on at least the user's particular role, location, or other context-type criteria, to a message notification engine, such as 126. In response to the user's query, the message notification engine 126 can determine a response to the query or set of instructions, and if needed, can communicate with a database, such as 130, or other data storage devices to obtain information in response to the query. The message notification engine 126 can return information based in part on at least the user's particular role, location, or other context-type criteria to the user via the client device 104a in response to the user query. The message notification engine 126 can also facilitate the display of a graphical representation of some or all of the information via a graphical user interface, such as 300, for an output device, such as 110. In this manner, a context sensitive response to a user's predefined query or set of instructions can be provided.

In yet another example, a response to a user query can return a different set of items when the initial query is processed at different times. For example, if an initial user query is for "empty" rooms in a particular health care environment, then a set of rooms which meets this condition, "empty," can change as one or more patients move into and out of rooms over a particular period of time. As a patient moves into or out of a room, location information associated with the particular patient can be received by a message notification engine, such as 126, and the message notification engine can process the location information. If, for instance, the message notification engine 126 facilitates a graphical display of a particular set of rooms on a graphical user interface, such as 300, as "empty," the message notification engine 126 can update and modify the set of rooms being displayed on the graphical user interface in real time as a change or modification to the query response occurs, i.e. the set of rooms that meets the "empty" condition.

In another embodiment, information provided in a query response can be modified, deleted, or updated based on an event, such as a completion event. If, for example, a piece of information is displayed in a graphical user interface, such as 300, an event may occur that determines when that piece of information is to be removed from the graphical user interface. Upon detection or determination that the particular event has occurred or is occurring, the particular piece of information can be removed from display on the graphical user interface. In this example, an event can be a completion-type event. A completion-type event can be, but is not limited to, an activity capable of being tracked by a health care information system such as admission, transfer, or discharge of a patient; an indication by a user via a client device that information should be removed; and expiration of a particular item over a predefined amount of time. A predefined amount of time can be, but is not limited to, a relative amount of time when a first display of information, such as 20 minutes; an absolute time such as midnight or 3:00 a.m.; or a calculation based at least in part on the information or context of the information, e.g. 15 minutes if not critical, or 60 minutes if critical.

In yet another embodiment, some or all information provided in a query response can be automatically modified, deleted, or updated based on time relative to an event. For instance, rather than a user indicate via a client device an occurrence or termination of a particular event to effect the removal of the information, a message notification engine, such as 126, can automatically or otherwise determine when to remove, modify, or update the information based on a relative time since initiation or start of an event.

In one embodiment, the appearance of a graphical representation of information, such as text or an icon, can change over a period of predefined time or upon detection, determination, or completion of an event. In one example, graphical information such as an icon can visually change appearance as time elapses. If, in this example, a user does not act or otherwise respond to a relatively critical event graphically represented by text or an icon, then the critical event can change color or change effects, e.g. start flashing or become animated, to indicate that attention of a user is needed. In yet another example, a graphical representation of information, such as text or an icon, can fade over a predefined period of time. In this instance, an icon representing a status of patient care or an event can be displayed in a graphical user interface, such as 300, with an initial opacity of approximately 100%. Over a predefined period of time, such as 24 hours, the icon can slowly fade to a relatively lower opacity such as approximately 25%. In this manner, graphical representation of the relative age of information such as a status of patient care or an event can be viewed in a graphical user interface.

In some embodiments, one or more users, such as 112, may desire to view information in more than one format. Embodiments of the present invention can display information in any number of desired formats, such as a geospatial view in the form of a map (shown in FIG. 3), or a view based on a selected subset of items such as rooms, patients or beds. Other selected subsets of information can be in the form of a user query over some or all of a population of items.

If a user query has been generated, or if information or a query response has been returned in response to a user query, a user can view the information or query response in a variety of different forms. For example, if a query response includes information, such as items, in a particular geographic area, then displaying the information and items in a graphical user interface including a map or geospatial view, such as 300 in FIG. 3, may be suitable since users may be accustomed to relating to such information or items in geographic-type terms. If the information and items in response to a query do not share a common geographic area, then other displays, views, or models can be used in accordance with embodiments of the invention. For instance, a suitable display, view, or model can include a grid or table view, where one or more items can be displayed in any number of rows and columns. In one example, up to six items or pieces of information could be displayed in a table or grid-type view comprising three columns and two rows. Any number of rows and columns can be displayed in a table or grid-type view in accordance with other embodiments of the invention.

Figure 4:
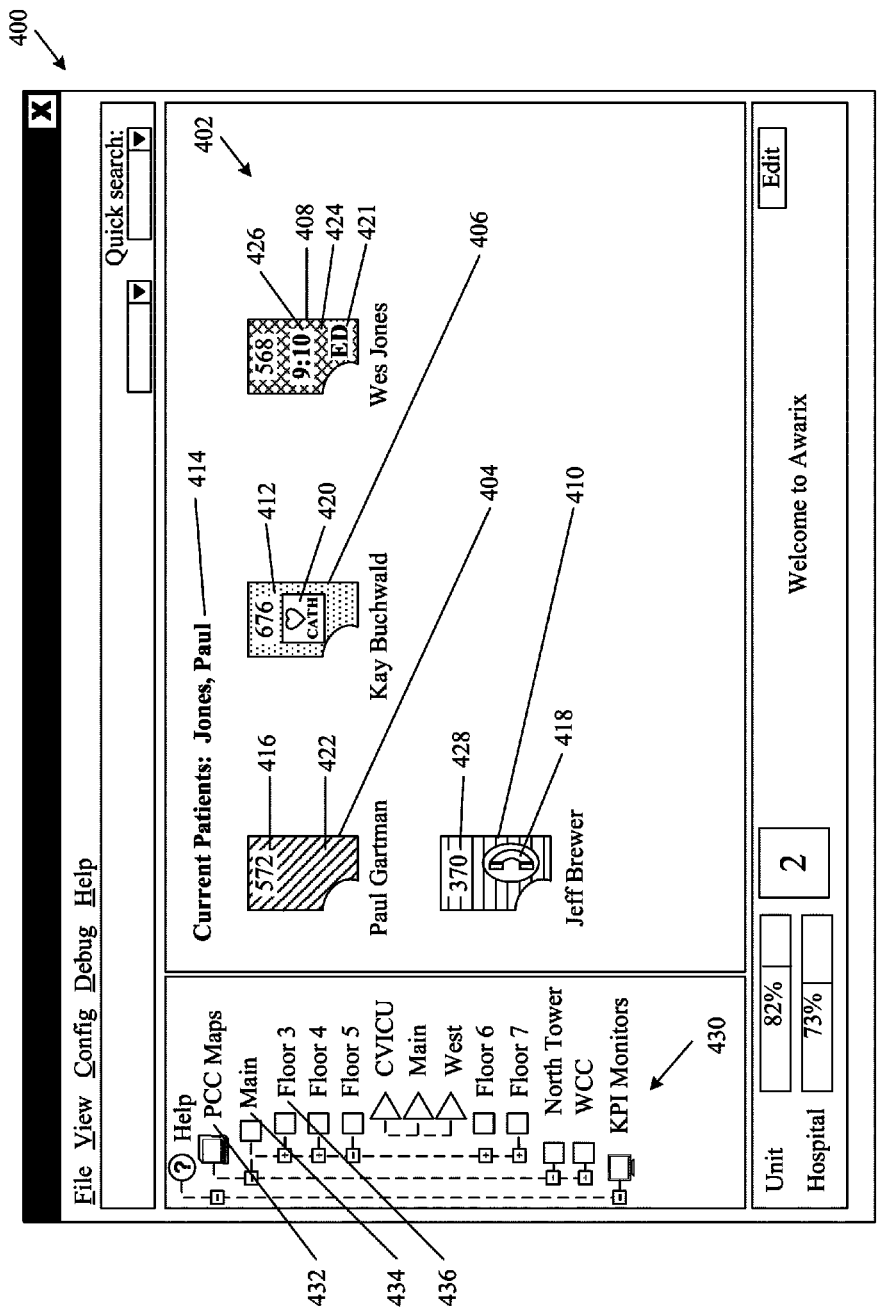
FIG. 4 is another graphical user interface in accordance with an embodiment of the invention.

FIG. 4 illustrates an example of another graphical user interface 400 for an output device in accordance with the invention. In the embodiment shown, an output device such as a display monitor can facilitate display of the graphical user interface 400. The graphical user interface 400 can include a table 402 or grid view of one or more items in a health care environment, such as a hospital. In the example shown, graphical representations of rooms 404, 406, 408, 410 can be displayed in response to a user query. One or more areas 412 within or adjacent to each of the graphical representations of each room 402 can display graphical information 414 associated with a notification of a message for a user or associated with a patient, or associated with a status of a particular patient, such as a location of a patient or a status of a patient's care. The areas 412 within each of the graphical representations of each room 404, 406, 408, 410 can include various types of graphical information including, but not limited to, text, icons, graphical elements, colors, timers, animation, or any combination thereof.

As an example, a query from a user can inquire whether patients of "Dr. Paul Jones" are currently in a particular hospital. The user, such as 112 in FIG. 1, can transmit the query via a client device, such as 104a, to the message notification engine, such as 126. The message notification engine 126 can process the query to determine a query response, and can communicate with the database 130 or other data storage device to receive or obtain information if needed. In response to the query, the message notification engine 126 can transmit a query response to the user 112 via the client device 104a. The message notification engine 126 can facilitate a display of the query response on a graphical user interface, such as 400, for an output device, such as 110. In the example shown in FIG. 4, a response to the user query can include a table 402 indicating that Dr. Jones has four patients in four respective rooms. Various graphical information can be displayed in the table including but not limited to, text, icons, graphical elements, colors, and animation. In this instance, graphical representations of each of the four rooms 404, 406, 408, 410 are displayed below text 414 indicating the doctor's name, "Jones, Paul." Respective areas 412 within each of the graphical representations of each room 404, 406, 408, 410 can display other text 416 indicating the respective room number for each patient, such as the text "572", "575", "568", and "370". Within two of the graphical representations of rooms 406, 410, respectively, are icons indicating a status of patient care for the particular patient in the room, such as a "phone" icon 418 indicating a case manager desires to speak to a doctor or other health care provider, and a "heart CATH" icon 420 indicating a patient in a cardiology lab or department.

In addition, a notification of a message for a user or associated with the patient can be displayed within or adjacent to a graphical representation of a room or other area. In the example graphical user interface 400 shown in FIG. 4, a notification indicating receipt of a message, such as an icon 421 with one or more letters, i.e. "ED", can be displayed adjacent to a room as previously described above. Other types of notifications and indicators of a notification can be displayed in a graphical user interface in accordance with embodiments of the invention.

Furthermore, a graphical element such as an outline 418 can highlight some or all of a particular room, such as 406, to indicate a special care state of a patient in the room. Rooms, such as 406, 408, shaded with a first color 422 such as green can indicate a patient in the particular room is an inpatient. A room, such as 410, shaded with a second color 424 such as blue can indicate a patient in a particular room is under observation or an observation patient. In addition, a timer 426 is displayed in one room, such as 410, to indicate how long a patient in a particular room has been in observation. A room, such as 412, can include animation 428 such as an alternating green-colored line pattern, which can represent that the patient's doctor has written a discharge order for the patient. Other types of graphical information can be used to represent information in a graphical user interface for an output device in accordance with embodiments of the invention. In this manner, a user can graphically view information associated with a notification of a message for a user or associated with a patient, as well as information associated with some or all of his or her patients including location information and a status of patient care for each patient.

In one embodiment, a user can generate and store multiple views of information, such as information that is interesting to the user. As needed, the user can store and retrieve each view as needed. In one embodiment, one or more views can be organized in a selection tree on a graphical user interface, such as 400, to allow user access and navigation to the various views. For example, as shown in FIG. 4, a selection tree 430 is positioned adjacent to the left portion of the view 402, The selection tree 430 shown includes a hierarchical structure with a root folder 432, shown here as "PCC", containing multiple building sub-folders 434, such as "MAIN", "North Tower", and "UVCC" for a particular health care facility. Each of the building sub-folders 434 include one or more building floors 436 or other area maps or views, for instance "Floor 3", "Floor 4", "Floor 5", "Floor 6", and "Floor 7". Each floor, area map or view can be further subdivided into sub-areas, shown here as "CVICU", "Main", and "West". Using an input device (not shown), such as a keyboard or a mouse, associated with a client device, such as 104, a user can access and navigate between some or all of the folders 432, sub-folders 434, and floors 436, areas, or other views. Other embodiments can include fewer or greater numbers of root folders, sub-folders, and floors or other areas depending on the configuration and layout of the health care environment of interest. In another embodiment, a map or geospatial-type view can include other configurations tree-type structures organized into multiple geographic areas, such as campus, building, floor, unit, etc.

With reference to FIG. 2, an example timeline for receiving a message and providing a message notification is as follows: A first user 219a, such as Nurse A, in room 202 may desire to transfer a patient 214 to a different room 204. Before the transfer can take place, a second user 219b, such as nurse B, in another room 208 should receive and accept a report associated with the patient 214, wherein the report describes the patient's basic health information along with any special notes. User 219a, or nurse A, can call a dedicated extension number via a communication device 221, and interact with an automated interactive voice response-type menu provided by the system 220. The system 220 can prompt the user 219a to enter keypad inputs via the communication device 221, such as inputting a room number associated with the room 204 the patient will be transferred to. The first user 219a can also record a message for the second user 219b, such as some or all of a patient report, and the user 219a ends the call.

The system 220 receives the information and message from the first user 219a, and the system can facilitate the display of a graphical user interface, such as 300 in FIG. 3, on one or more output devices 228, 230, 232, 234 of a "report ready" icon adjacent to or within a representation of the room 204 the patient will be transferred to. When the second user 219b or nurse B, finishes his or her current task, the user 219b can view an output device, such as 232, and observe the "report ready" icon adjacent to or within a representation of the room 204 the patient will be transferred to. The second user 219b or nurse B can dial the dedicated extension number via another communication device 225, and interact with an automated interactive voice response-type menu provided by the system 220. The second user 219b can retrieve and listen to the message from the first user 219a or nurse A, and perform any acts necessary in response to the message. Upon the second user's receipt of the message, the system 220 can update some or all of the output devices 228, 230, 232, 234 by updating or removing the "report ready" icon adjacent to or within a representation of the room 204 the patient will be transferred to.

In this example, if the first user 219a or nurse A can view an output device, such as 228, and see the update or removal of the "report ready" icon from the graphical user interface, then the first user 219a or nurse A can receive an acknowledgement or confirmation that her message was accepted by the second user 219b or nurse B when the "report ready" icon is updated or removed by the system 220. In this manner, the sender can obtain a message receipt notification or confirmation.

Figure 5:
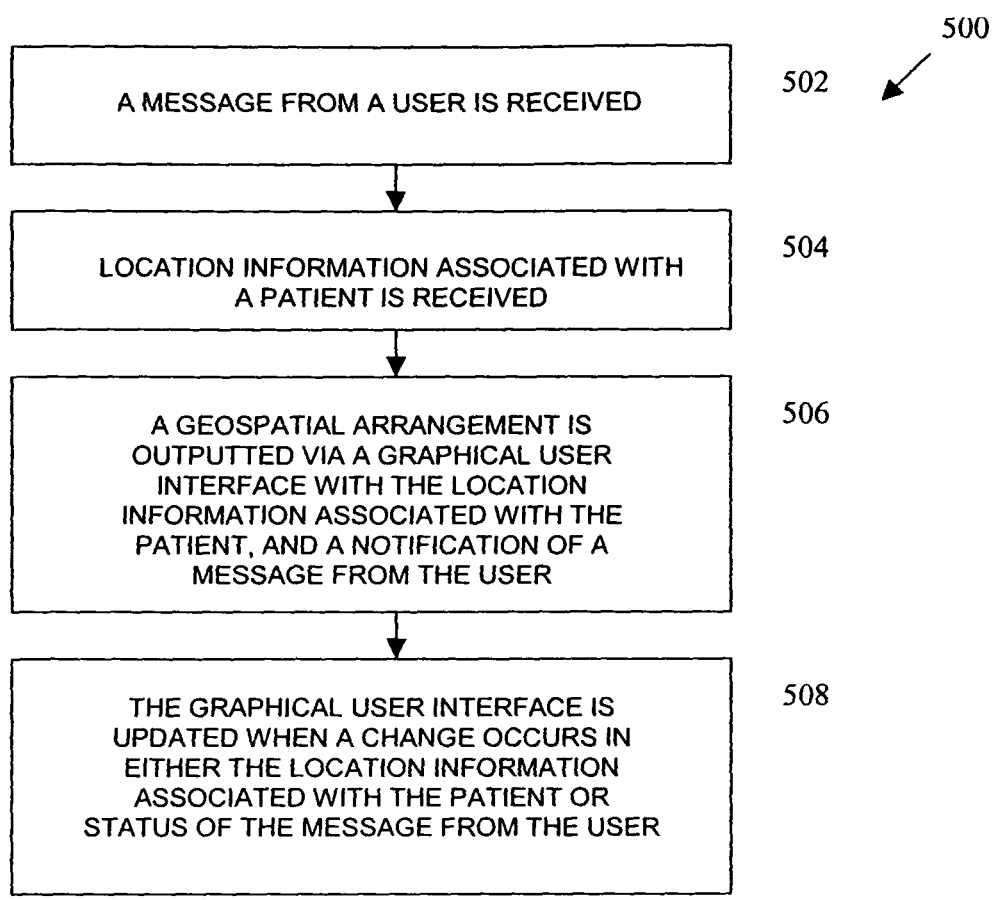
FIG. 5 is a flowchart diagram of an exemplary method in accordance with an embodiment of the invention.

FIG. 5 is a flowchart for an exemplary method in accordance with an embodiment of the invention. The method 500 shown can provide a message notification associated with care of a patient in a health care environment. The method 500 can be implemented by the system 100 shown in FIG. 1. Other methods in accordance with embodiments of the invention can have fewer or additional steps than the method 500 described below.

The method 500 begins in block 502. In block 502, a message from a source is received. A source can include a user, person, entity, machine, or device. In other embodiments, a message can be an automated message received from a device or machine.

Block 502 is followed by block 504, in which location information associated with a patient is received.

Block 504 is followed by block 506, in which a geospatial arrangement is outputted via a graphical user interface with the location information associated with the patient, and a notification of a message from the user.

Block 506 is followed by block 508, in which the graphical user interface is updated when a change occurs in either the location information associated with the patient or status of the message from the source. The method 500 ends at block 508.

Figure 6:
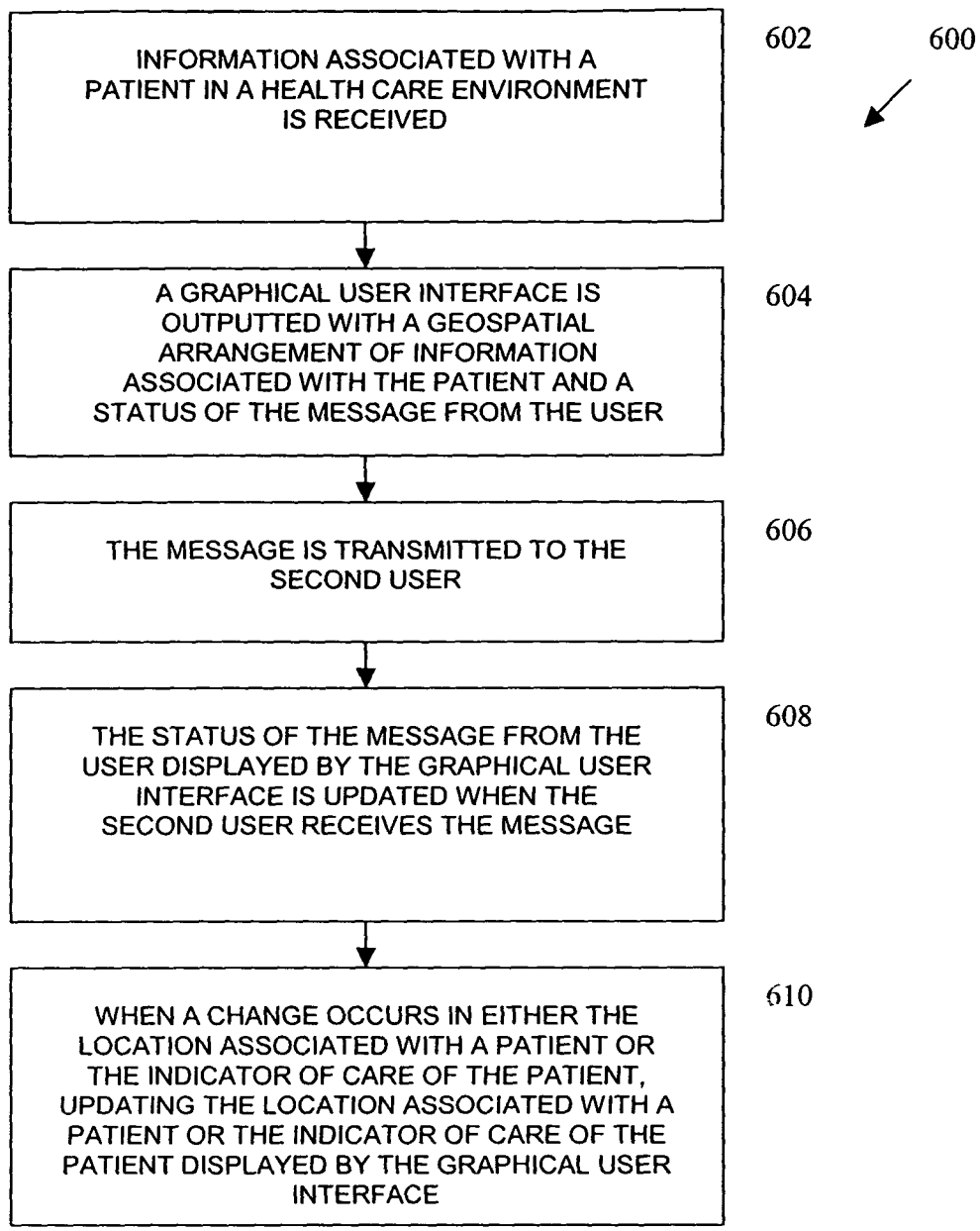
FIG. 6 is a flowchart diagram of another method in accordance with an embodiment of the invention.

FIG. 6 is a flowchart for another method in accordance with an embodiment of the invention. The method 600 shown can provide a message in a health care environment. The method 600 can be implemented by the system 100 shown in FIG. 1. Other methods in accordance with embodiments of the invention can have fewer or additional steps than the method 600 described below.

The method 600 begins in block 602. In block 602, information associated with a patient in a health care environment is received. The information can include a message from a source, a user, a person, an entity, or an automated message from a device or machine.

Block 602 is followed by block 604, in which a graphical user interface is outputted with a geospatial arrangement of information associated with the patient and a status of the message from the source.

Block 604 is followed by block 606, in which the message is transmitted to the user.

Block 606 is followed by block 608, in which the status of the message from the source displayed by the graphical user interface is updated when the user receives the message. The method 600 ends at block 608.

While the above description contains many specifics, these specifics should not be construed as limitations on the scope of the invention, but merely as exemplifications of the disclosed embodiments. Those skilled in the art will envision many other possible variations within the scope of the invention as defined by the claims appended hereto.

The invention claimed is:

1. A method comprising executing computer implemented instructions performed by one or more processors for providing a message notification associated with real-time care of a patient in a health care environment, the method comprising:
receiving, via at least one processor, a message from a source, wherein the message is associated with a voice or data communication to a user;
receiving, via at least one processor, location information associated with a plurality of patients;
receiving, via at least one processor, patient care information from at least one of the following information systems: an ordering system, a result reporting system, a lab-type system, a pharmacy-type system, a radiology-type system, a transcription-type system, an environmental services-type system, or a transportation-type system;
outputting in a geospatial map via a graphical user interface associated with a display mounted in the health care environment the location information associated with the plurality of patients and the patient care information, wherein the geospatial map comprises a scaled map of the health care environment, and a notification of the message from the source, wherein the notification corresponds with message content or retrieval of the message;
updating, via at least one processor, the graphical user interface when: (i) a change occurs in the location information associated with at least one of the plurality of patients, (ii) a change occurs in the patient care information and (iii) when a change occurs in the status of the message from the user;
receiving a user query that comprises a request to display on the geospatial map via the graphical user interface the location information associated with a subset of the plurality of patients receiving care from a physician in the health care environment based on a particular user role, wherein the particular user role comprises at least one of: (i) a physician, (ii) a nurse or (iii) a health care assistant;
receiving, based at least in part on the user query, a query response that comprises the requested location information for each of the one or more patients in the subset; and
outputting, in response to the user query, the location information associated with each of the one or more patients in the subset on the geospatial map via the graphical user interface, wherein the location information comprises one or more indicators that are displayed adjacent to one or more patient rooms associated with each of the one or more patients in the subset.

2. The method of claim 1, wherein receiving a message from a source comprises at least one of the following: receiving a message from a user, receiving a voice mail message, receiving an automated message from a device or machine, receiving a message via an interactive voice response system, receiving an email message, or receiving a text message.

3. The method of claim 1, wherein the message comprises at least one of the following: a voice mail, a text-to-speech message, an email message, or a pre-recorded message.

4. The method of claim 1, wherein receiving location information associated with the plurality of patients comprises at least one of the following: detecting a radio frequency identification device adjacent to the patient; or receiving a signal from a radio frequency identification device adjacent to a patient chart associated with the patient.

5. The method of claim 1, wherein the geospatial map comprises at least one of the following: a map representing at least a portion of the health care environment; a map with an actual aspect ratio, door location, and orientation of a floor or a building associated with the health care environment; one or more non-bed objects or persons in a room of the health care environment; or a geospatial-type view of at least a portion of the health care environment.

6. The method of claim 1, wherein a notification of a message from a source comprises at least one of the following: text, an icon, a graphical element, a color, a timer, a sound, or animation.

7. The method of claim 1, wherein the health care environment comprises at least one of the following: a room, a building, a hospital, an assisted care facility, or a medical care facility.

8. A method comprising executing computer implemented instructions performed by one or more processors for providing a message in a health care environment, the method comprising:
receiving, via at least one processor, location information associated with a plurality of patients in a health care environment, comprising:
a message from a source, wherein the message is associated with a voice or data communication to a user; and
patient care information in a HL7 standard format from at least one of the following: an ordering system, a result reporting system, a lab-type system, a pharmacy-type system, a radiology-type system, a transcription-type system, an environmental services-type system, or a transportation-type system;
outputting via a graphical user interface associated with a display mounted in the health care environment a geospatial map of the location information associated with the plurality of patients, the patient care information, and a notification of and a status of the message from the source, wherein the geospatial map comprises a scaled map of the health care environment, and wherein the notification corresponds with message content or retrieval of the message;
transmitting, via at least one processor, the message to the user;
updating, via at least one processor, the status of the message from the source displayed by the graphical user interface when the user receives the message;
updating, via at least one processor, the graphical user interface when: (i) a change occurs in the location information associated with at least one of the plurality of patients, (ii) a change occurs in the patient care information and (iii) when a change occurs in the status of the message from the source;
receiving a user query that comprises a request to display on the geospatial map via the graphical user interface the location information associated with a subset of the plurality of patients receiving care from a physician in the health care environment based on a particular user role, wherein the particular user role comprises at least one of: (i) a physician, (ii) a nurse or (iii) a healthcare assistant;
receiving, based at least in part on the user query, a query response that comprises the requested location information for each of the one or more patients in the subset; and
outputting, in response to the user query, the location information associated with each of the one or more patients in the subset on the geospatial map via the graphical user interface, wherein the location information comprises one or more indicators that are displayed adjacent to one or more patient rooms associated with each of the one or more patients in the subset.

9. The method of claim 8, wherein the location information associated with the plurality of patients comprises at least one of the following: a signal received from a radiofrequency identification device adjacent to the patient; detection of a radiofrequency identification device adjacent to the patient; or a signal received from a radio frequency identification device adjacent to a patient chart associated with the patient.

10. The method of claim 8, wherein the message comprises at least one of the following: a voice mail, a text-to-speech message, or a pre-recorded message.

11. The method of claim 8, wherein transmitting the message to the user comprises at least one of the following: facilitating receipt of a voice mail message; facilitating receipt of a message via an interactive voice response system.

12. The method of claim 8, wherein the geospatial map comprises at least one of the following: a map representing at least a portion of the health care environment; a map with an actual aspect ratio, door location, and orientation of a floor or a building associated with the health care environment; one or more non-bed objects or persons in a room of the health care environment; or a geospatial-type view of at least a portion of the health care environment.

13. A system for providing a message notification associated with care of a plurality of patients in a health care environment, comprising:
an output device capable of displaying a geospatial map via a graphical user interface a location associated with a plurality of patients and a status of a message from a source, wherein the output device comprises a display mounted in the health care environment, and wherein the message is associated with a voice or data communication to a user; and
a message notification engine capable of
receiving a message from a source;
receiving information associated with the plurality of patients in a health care environment, comprising:
the location associated with each of the plurality of patients; and
real time patient care information in at least one HL7 standard format from at least one of the following information systems: an ordering system, a result reporting system, a lab-type system, a pharmacy-type system, a radiology-type system, a transcription-type system, an environmental services-type system, or a transportation-type system;
outputting via the output device the location associated with each of the plurality of patients, the patient care information, and a notification of and a status of the message from the source, wherein the notification corresponds with message content or retrieval of the message;
providing access to the user to receive the message from the source;
when a change in the status of the message from the source occurs, updating the graphical user interface;

updating, via the output device, the graphical user interface when: (i) a change occurs in the location associated with at least one of the plurality of patients, (ii) a change occurs in the patient care information and (iii) when a change occurs in the status of the message from the source;

receiving a user query that comprises a request to display on the geospatial map via the graphical user interface the location associated with a subset of the plurality of patients receiving care from a physician in the health care environment based on a particular user role, wherein the particular user role comprises at least one of: (i) a physician, (ii) a nurse or (iii) a healthcare assistant;

receiving, based at least in part on the user query, a query response that comprises the requested location associated with each of the one or more patients in the subset; and outputting, in response to the user query, the location associated with each of the one or more patients in the subset on the geospatial map via the graphical user interface, wherein the location comprises one or more indicators that are displayed adjacent to one or more patient rooms associated with each of the one or more patients in the subset.

14. The system of claim 13, wherein the message comprises at least one of the following: a voice mail, a text-to-speech message, an email message, or a pre-recorded message.

15. The system of claim 13, wherein the graphical user interface comprises a map of the health care environment with an actual aspect ratio, door location, and orientation of a floor or a building in the health care environment; or one or more non-bed objects or persons in a room of the health care environment.

16. The system of claim 13, wherein receiving a message from a source comprises at least one of the following: receiving a message from a user; receiving a voice mail message; receiving an automated message from a device or machine; or receiving a message via an interactive voice response system.

17. The system of claim 13, wherein receiving the location associated with the plurality of patients in a health care environment comprises at least one of the following: receiving a signal received from a radio frequency identification device adjacent to the patient; detecting a radio frequency identification device adjacent to the patient; receiving a signal from a radio frequency identification device adjacent to a patient chart associated with the patient; or receiving input from a user via a client device.

18. The system of claim 13, wherein providing access to a user to receive the message from the source comprises at least one of the following: facilitating receipt of a voice mail message; or facilitating receipt of a message via an interactive voice response system.

19. A system comprising:

a query support engine in communication with at least one network, wherein the query support engine receives real-time patient care information in at least one HL7 standard format from at least one of the following information systems: an ordering system, a result reporting system, a lab-type system, a pharmacy-type system, a radiology-type system, a transcription-type system, an environmental services-type system, or a transportation-type system; and a display device in communication with the query support engine, the public-type display device comprising a user interface for providing a message notification associated with care of a patient in a health care environment, the display device comprising:

a geospatial map of a health care environment, wherein the map comprises at least one or more persons in a room of the health care environment and an actual aspect ratio, door location, and orientation of a floor or a building in the health care environment;

at least one indicator associated with a location of a plurality of patients in the health_care environment; and at least one indicator of a message from a source, wherein the at least one indicator corresponds with message content or retrieval of the message, and wherein the message is associated with a voice or data communication to a user;

receiving a user query that comprises a request to display on the geospatial map via the user interface the location associated with a subset of the plurality of patients receiving care from a physician in the health care environment based on a particular user role, wherein the particular user role comprises at least one of: (i) a physician, (ii) a nurse or (iii) a health care assistant;

receiving, based at least in part on the user query, a query response that comprises the requested location associated with each of the one or more patients in the subset; and outputting, in response to the user query, the location associated with each of the one or more patients in the subset on the geospatial map via the graphical user interface, wherein the location comprises one or more indicators adjacent to one or more patient rooms associated with each of the one or more patients in the subset.

20. The system of claim 19, wherein the geospatial map of a health care environment comprises a graphical representation of a plurality of rooms in the health care environment.

21. The system of claim 19, wherein the geospatial map of the health care environment can be updated when a change occurs to the status of the message from the source.

* * * * *